(12) United States Patent
Ehrenkranz

(10) Patent No.: US 10,613,082 B2
(45) Date of Patent: Apr. 7, 2020

(54) DEVICE FOR PERFORMING A DIAGNOSTIC TEST AND METHODS FOR USE THEREOF

(71) Applicant: i-CalQ, LLC, Salt Lake City, UT (US)

(72) Inventor: Joel R. L. Ehrenkranz, Salt Lake City, UT (US)

(73) Assignee: i-calQ, LLC, Salt Lake City, UT (US)

( * ) Notice: Subject to any disclaimer, the term of this patent is extended or adjusted under 35 U.S.C. 154(b) by 0 days.

(21) Appl. No.: 16/196,787

(22) Filed: Nov. 20, 2018

(65) Prior Publication Data

US 2019/0086400 A1 Mar. 21, 2019

Related U.S. Application Data

(62) Division of application No. 13/862,176, filed on Apr. 12, 2013, now Pat. No. 10,132,802.

(60) Provisional application No. 61/625,368, filed on Apr. 17, 2012, provisional application No. 61/740,975, filed on Dec. 21, 2012.

(51) Int. Cl.
| | |
|---|---|
| *G01N 33/543* | (2006.01) |
| *G01N 21/84* | (2006.01) |
| *G01N 33/558* | (2006.01) |
| *G01N 33/49* | (2006.01) |

(52) U.S. Cl.
CPC ... *G01N 33/54366* (2013.01); *G01N 21/8483* (2013.01); *G01N 33/558* (2013.01); *G01N 33/4915* (2013.01)

(58) Field of Classification Search
None
See application file for complete search history.

(56) References Cited

U.S. PATENT DOCUMENTS

| | | | | |
|---|---|---|---|---|
| 2006/0222567 A1* | 10/2006 | Kloepfer | ............... | G01N 21/78 422/68.1 |
| 2008/0038711 A1* | 2/2008 | Curry | .................. | G01N 33/582 435/4 |
| 2010/0312137 A1* | 12/2010 | Gilmour | .............. | G01N 33/558 600/551 |

* cited by examiner

*Primary Examiner* — Rebecca L Martinez
(74) *Attorney, Agent, or Firm* — Magleby Cataxinos & Greenwood

(57) ABSTRACT

Assay cassettes and testing devices that can be used to provide rapid, accurate, affordable, laboratory-quality testing at the point of care. Such assay cassettes and testing devices are designed to provide rapid, quantitative test results in a point-of-care setting or the like. Likewise, such assay cassettes and testing devices may eliminate or replace expensive, centralized clinical testing equipment and technical personnel. Such testing device may include automated data reporting and decision support. Methods for performing point of care diagnostic tests are also disclosed.

4 Claims, 9 Drawing Sheets

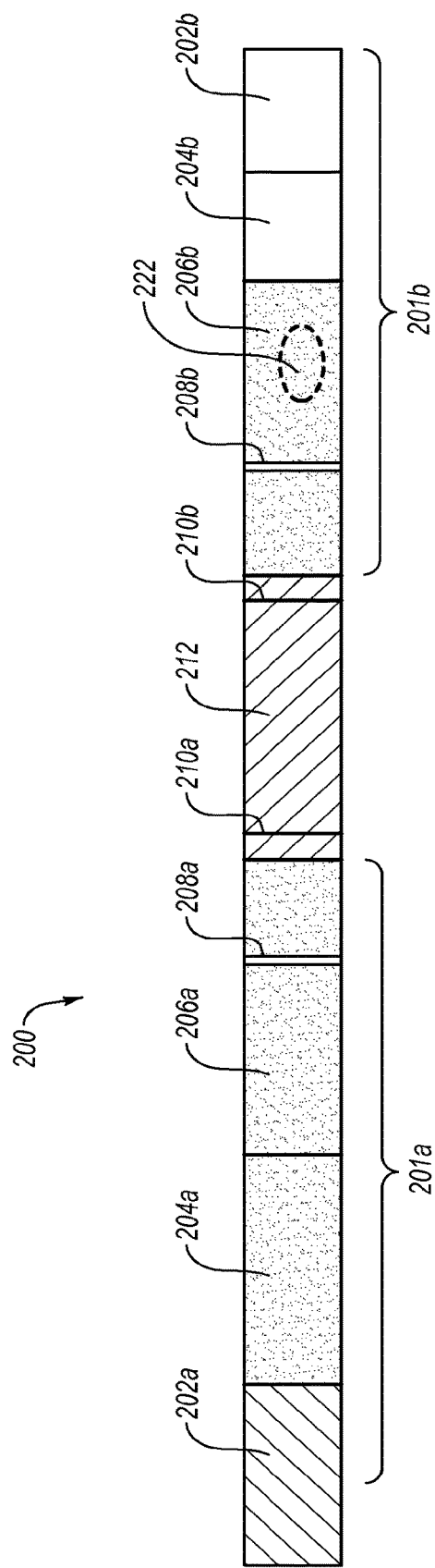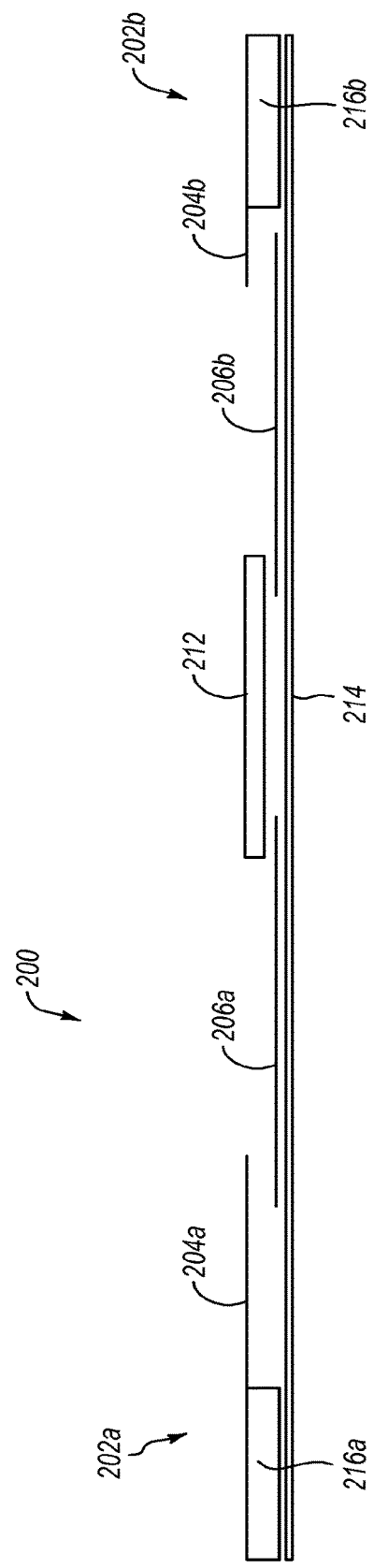
Fig. 2A
Fig. 2B

DEVICE FOR PERFORMING A DIAGNOSTIC TEST AND METHODS FOR USE THEREOF

CROSS-REFERENCE TO RELATED APPLICATIONS

This application is a divisional of application U.S. patent application Ser. No. 13/862,176 filed Apr. 12, 2013, which claims the benefit of and priority to U.S. Provisional Patent Application No. 61/625,368 filed Apr. 17, 2012 and U.S. Provisional Patent Application No. 61/740,975 filed Dec. 21, 2012, the entireties of which are incorporated herein by reference.

BACKGROUND

Sampling and testing of biological samples and body fluids (e.g., saliva, blood, urine, fecal matter, foods, plants, fish, minerals, animals, etc.) is common for both testing and monitoring humans, fish, animals, and plants for any number of biochemical or physiological conditions and, of course, for determining the general state of health of an organism. For example, sampling and testing of human body fluids is often performed for point-of-care testing ("POCT"). POCT is defined as medical testing at or near the site of patient care. The driving notion behind POCT is to perform and provide the test conveniently and immediately to the patient. This increases the likelihood that the patient, physician, and care team will receive the results more quickly and allows for immediate clinical management decisions to be made. POCT examples include, but are not limited to, blood glucose testing, metabolic testing (e.g., thyroid stimulating hormone), blood gas and electrolytes analysis, rapid coagulation testing, rapid cardiac markers diagnostics, drugs of abuse screening, urine testing, pregnancy testing, fecal occult blood analysis, food pathogen screening, hemoglobin diagnostics, infectious disease testing, cholesterol screening, cancer testing (e.g. PSA), hormone testing (hCG, LH, FSH), cardiac (troponin), pulmonary, gastroenterology (e.g., *H. pylori* antibodies), urology, dermatology, neurology, pediatrics, surgical, and public health (Ebola, cholera, HIV), testing and combinations thereof.

One testing method that is often employed for POCT and more conventional testing involves the use of lateral-flow chromatographic immunoassay cassettes. Lateral-flow chromatographic immunoassay cassettes can be used to easily and quickly obtain a variety of qualitative results relating to a number of biochemical and physiological conditions and disease states of an individual. These kinds of tests require the end user to simply add a sample to the cassette and then observe the result a few minutes later. Since such rapid and easy-to-use tests are user friendly, they are very popular in both the professional and consumer markets nowadays. Such tests are also widely used in areas where access to trained health care professionals is limited or where access to proper medical facilities is limited (e.g., poor areas, developing countries, war zones, etc.).

Lateral flow chromatographic immunoassay methods and devices have been described extensively. See, e.g., Gordon and Pugh, U.S. Pat. No. 4,956,302; H. Buck, et al., WO 90/06511; T. Wang, U.S. Pat. No. 6,764,825; W. Brown, et al., U.S. Pat. No. 5,008,080; Kuo and Meritt, U.S. Pat. No. 6,183,972, EP 00987551A3. Such assays involve the detection and determination of an analyte substance that is a member of a specific binding pair consisting of a ligand and a receptor. The ligand and the receptor are related in that the receptor specifically binds to the ligand, being capable of distinguishing a specific ligand or ligands from other sample constituents having similar characteristics. Immunological assays involving reactions between antibodies and antigens are one such example of a specific binding assay. Other examples include DNA and RNA hybridization reactions and binding reactions involving hormones and other biological receptors. One well-known commercial embodiment of this technique is the Clearblue One-Step Pregnancy Test.

Lateral flow chromatographic immunoassay test cassettes have a number of desirable characteristics including their ease of use and broad applicability to a variety of analytes. Likewise, immunoassay procedures capable of being carried out on a test strip and which can be administered in the field or other locations where medical testing laboratories are not readily available have provided a great benefit to the diagnosis and control of disease. Currently, however, such lateral flow chromatographic immunoassay tests are generally only capable of providing qualitative results. That is, while currently available lateral flow chromatographic immunoassay test cassettes and cassette reader apparatuses are particularly well-suited for telling a practitioner whether or not one or more test substances are present in a sample above a given detection limit, they are poorly suited for providing quantitative results. There is an ongoing need in the art for devices and methods that combine the ease of use characteristics of lateral flow chromatographic immunoassay tests with systems that are designed to provide quantitative results. Such devices and methods may, for example, allow medical practitioners to diagnose, monitor, and manage a variety of conditions at the point of care (e.g., chair-side or essentially anywhere in the world) without being tied to a medical facility or a testing laboratory.

BRIEF SUMMARY

Devices and methods for performing point of care diagnostic tests for detecting and quantifying at least one analyte in a biological sample (e.g., a body fluid). Disclosed herein are assay cassettes and testing devices that can be used to provide rapid, accurate, affordable laboratory-quality testing at the point of care. Such assay cassettes and testing devices are designed to provide rapid, quantitative test results in a point-of-care setting or the like where, in the past, only qualitative or semi-quantitative results have typically been available. Likewise, such assay cassettes and testing devices may eliminate or replace expensive, centralized clinical testing equipment and technical personnel. Such testing devices may include automated data reporting and decision support.

In one embodiment, a diagnostic test system is disclosed. The system includes a lateral-flow chromatographic assay cassette and a compact, portable testing device that includes data collection and data analysis capabilities. The testing device is configured to interface with and analyze output of the lateral-flow chromatographic assay cassette.

In one embodiment, the lateral-flow chromatographic assay cassette may include a capture ligand capable of capturing and localizing at least one analyte of interest in a sample on an analysis surface of the lateral-flow chromatographic assay cassette, at least one reporter configured for interacting with at least one of the analyte of interest or the capture ligand, and at least a first calibration standard and a second calibration standard configured to provide at least a two-point calibration curve.

In another embodiment, the lateral flow chromatographic assay cassette may include a test strip and a separate calibration strip. In this embodiment of a lateral flow chromatographic assay cassette, a test sample (i.e., a sample containing an unknown amount of an analyte of interest) may be run in parallel with a calibration standard (i.e., a sample containing a known amount of the analyte of interest). The response to the known amount of the analyte of interest in the calibration standard on the lateral flow immunoassay device may be used to generate a calibration curve that can be used to quantify the amount of the analyte of interest in the test sample.

The lateral flow chromatographic assay cassette that includes a test strip and a separate calibration strip cassette may include a base, an absorbent test strip for analyzing an analyte of interest in an experimental sample positioned above the base, and an absorbent calibration strip for running at least one calibration standard positioned above the base in proximity to the absorbent test strip. The device further includes a first sample application zone positioned between a distal end and a proximal end the first absorbent strip, and a second sample application zone positioned between a distal end and a proximal end of the second absorbent strip. A volume of a liquid test sample applied to the first sample application zone and a volume of a liquid calibration standard applied or deposited to the second sample application zone each diffuse (i.e., wick) through their respective absorbent strips from the distal end to the proximal end. Accordingly, the analyte of interest, if present in the experimental sample, and the calibration standard interact with at least a first reporter (e.g., an antibody) immobilized on the first and second absorbent strips to yield a detectable signal.

The testing device includes a testing apparatus that is configured for collecting data from the lateral-flow chromatographic assay cassette. In one embodiment, the testing device includes a testing apparatus that is configured to be physically coupled to a handheld device (e.g., a smartphone). The testing apparatus couples the lateral-flow chromatographic assay cassette to the handheld device in proximity to a light source, the light source being capable of transmitting at least one wavelength of light configured to yield a detectable signal from the reporter(s), and a detector positioned to capture the detectable signal from the reporter(s). In another embodiment, the testing apparatus may be a stand-alone device that includes its own light source, optics, data capture capabilities, and the like. In such an embodiment, the testing apparatus may be configured to collect assay data from an assay cassette and transfer it to a handheld device (e.g., a smartphone) for analysis and reporting.

In addition, the system described herein may include an interpretive algorithm stored in a computer readable format and electronically coupled to a handheld device, wherein the interpretive algorithm is configured to (i) calculate a calibration curve based on at least one of a the first calibration standard and the second calibration standard or a known amount of an analyte of interest and a blank region and then (ii) convert the detectable signal from the reporter(s) to a numerical value related to the presence or amount of the at least one analyte present in a sample. The interpretive algorithm may be included in an on-board computing system of the handheld device or the interpretive algorithm may be stored remotely in a computer storage medium that is accessible by the handheld device.

In another embodiment, a method for detecting at least one analyte of interest in a sample is disclosed. The method includes (1) providing a lateral-flow chromatographic assay cassette as described herein above, (2) providing a testing device as described herein above, and (3) applying a liquid sample that includes at least one analyte of interest to the lateral-flow chromatographic assay cassette. The method further includes (4) inserting the lateral-flow chromatographic assay cassette into the testing apparatus, (5) illuminating the lateral-flow chromatographic assay cassette with the light source of the handheld device in order to yield a detectable signal from the reporter(s), and (6) querying the interpretive algorithm for (i) calculating the calibration curve and then (ii) converting the detectable signal from a first reporter to a numerical value related to the presence or amount of the at least one analyte present in a sample.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 2A and 2B illustrates a lateral flow immunoassay device according to one embodiment of the present invention;

DETAILED DESCRIPTION

Devices and methods for performing point of care diagnostic tests for detecting and quantifying at least one analyte in a biological sample (e.g., a body fluid). Disclosed herein are assay cassettes and testing devices that can be used to provide rapid, accurate, affordable laboratory-quality testing at the point of care. Such assay cassettes and testing devices are designed to provide rapid, quantitative test results in a point-of-care setting or the like where, in the past, only qualitative or semi-quantitative results have typically been available. Likewise, such assay cassettes and testing devices may eliminate or replace expensive, centralized clinical testing equipment and technical personnel. Such testing device may include automated data reporting and decision support.

In one embodiment, a diagnostic test system is disclosed. The system includes a lateral-flow chromatographic assay cassette and a testing device that includes data collection and data analysis capabilities. The testing device is configured to interface with and analyze output of the lateral-flow chromatographic assay cassette.

I. Diagnostic Test Systems

Figure 1:
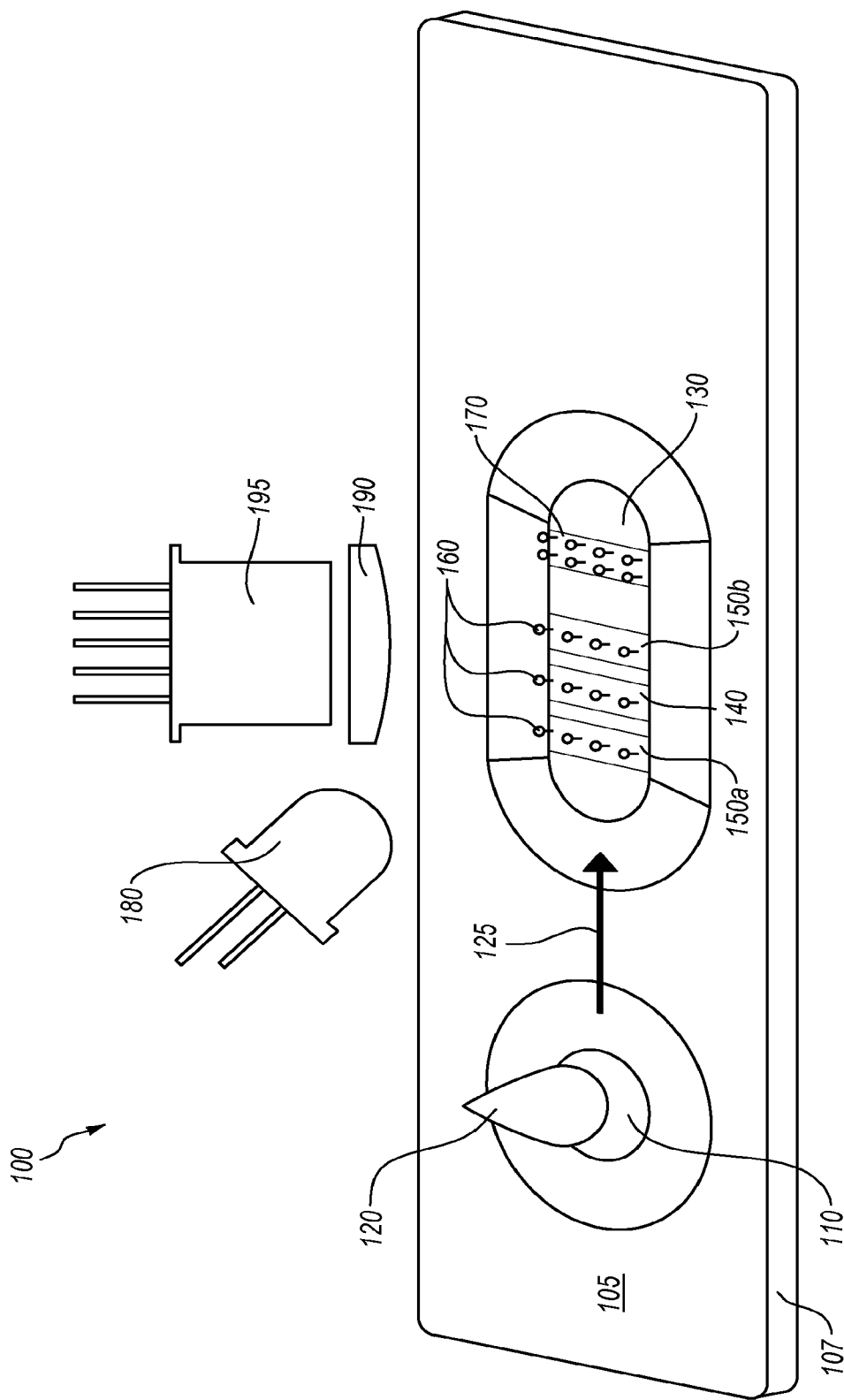
FIG. 1 illustrates a perspective view of a diagnostic test system, according to one embodiment of the present disclosure.

Referring to FIG. 1, perspective view of a diagnostic test system 100 is illustrated. The diagnostic test system 100 includes a lateral-flow chromatographic assay cassette 105 and means for collecting assay data from the lateral-flow chromatographic assay cassette 105.

The lateral-flow chromatographic assay cassette 105 includes a plastic housing 107 containing a test strip, which is generally a plastic strip laminated with porous material that permits lateral flow of liquid. The illustrated lateral-flow chromatographic immunoassay cassette 105 includes a sample application zone 110 and an analysis zone 130.

When a sample 120 is applied to the lateral-flow chromatographic immunoassay cassette 105 at the sample application zone 110, the sample 120 diffuses through the strip in flow direction 125 toward the analysis zone 130. In the embodiment illustrated in FIG. 1, the analysis zone 130 includes a test line 140 that includes at least one capture ligand selected for capturing at least one analyte of interest in the sample 120. The analysis zone 130 further includes at least first and second calibration standard lines 150a and 150b. Additionally, the analysis zone may include a positive control line 170 that may be configured to provide an indication regarding whether or not sample has diffused though the strip and whether or not the assay is functioning. For example, the positive control line 170 may include a water soluble dye that is positioned and configures to indicate that the sample has flowed the length of/travered the test strip.

The analyte(s) of interest, the first and second calibration standards, and the positive control can be detected on their various target lines, 140, 150a, 150b and 170, respectively, with various reporters. The reporters 160 for each of the various target lines, 140, 150a, 150b and 170, may be the same or different. Examples of suitable reporters include, but are not limited to, visible and fluorescent dyes, latex beads, enzymes, gold nanoparticles, silver nanoparticles, titanium nanoparticles, europium fluorophores, quantum dots, and the like. Quantum dots are nano-scale materials that can produce excited emission at particular wavelengths depending on their size and shape. Quantum dots can be used in immunoassays where dyes have traditionally been used. However, quantum dots are generally superior to traditional organic dyes on several counts: quantum dots are typically much brighter that organic dyes (owing to their high extinction coefficients combined with a comparable quantum yield to fluorescent dyes) as well as their stability (i.e., much less photobleaching). For example, it has been estimated that quantum dots are 20 times brighter and 100 times more stable than traditional fluorescent reporters.

Emission from the various reporters can be excited by a number of sources. In the illustrated embodiment, an LED light source 180 is used illuminate the analysis zone 130 of the lateral flow assay cassette 105. Illumination by the light source 180 may produce a detectable signal that includes at least one of emission (e.g., fluorescence), color, reflectance, diffuse scattering (i.e., scattering and absorbance), elastic light scattering, chemiluminescence, chemifluorescence, transmission, plasmon surface resonance, or absorbance from the reporters. A lens 190 (e.g., a collimating lens) and a detector 195 (e.g., a CCD or CMOS camera) are used to collect data from the reporters and the first and second calibration standards.

When the sample 120 is applied to the diffusion strip of the lateral-flow chromatographic assay cassette 105, the liquid in the sample carries the analyte of interest through the diffusion strip in flow direction 125 into the analysis zone 130 where it can be captured by the capture ligand line 140. The first and second calibration standard lines 150a and 150b are selected to provide a detectable signal that correlate to non-zero concentration values of the analyte of interest. For example, the first and second calibration standard lines 150a and 150b may include an amount of the analyte of interest or another material pre-bound to the diffusion strip of the lateral-flow chromatographic assay cassette 105. The reporter 160 may be a diffusible material that can bind to the capture ligand line 150 and the first and second calibration standards 150a and 150b in an amount proportional to the amount of bound ligand is present in each line. In response to illumination by the light source, the reporter 160 bound to each of lines 140, 150a, and 150b provides a signal that can be used to calculate a calibration curves and, in turn, determine the concentration of the analyte of interest in the sample 120. A more detailed discussion of methods for deriving analyte concentration from the data of the first and second calibration standards 150a and 150b and the capture line 140 is discussed in greater detail elsewhere herein.

In one type of lateral-flow chromatographic immunoassay cassette, the test strip is divided into four domains, which can be made of only one kind of material or several kinds of material (e.g., up to four different kinds of materials). The first domain is for sample addition. It functions to remove viscous and particulate materials in the sample and also to condition the sample solution for the reactions in the following domains. The second domain is a mobile-phase with a color conjugate. In one embodiment, the color conjugate may be made from conjugation between a visible color marker (e.g., colored beads, colloidal gold, fluorescent dyes, etc.) and a detection antibody. The detection antibody can bind a specific antigen in the sample (e.g., an analyte of interest or a positive control substance) and forms an antigen-color conjugate complex. The third domain of the lateral-flow chromatographic immunoassay cassette is a solid-phase with immobilized capture antibody. The capture antibody can bind the antigen of the antigen-color conjugate complex and forms capture antibody-antigen-color conjugate complex sandwich. The fourth domain is for solution absorption. It draws sample solution towards it continuously.

During the testing, sample added to the first domain flows to the second domain. If the antigen is present in the sample, it will bind the color conjugate to form antigen-color conjugate complex. This complex then migrates to the third domain to bind the capture antibody and forms the capture antibody-antigen-color conjugate complex sandwich. Since the capture antibody is immobilized in the third domain, the sandwich shows as a visible color signal or a fluorescent signal, depending on the dye type, on the site of the capture antibody. If there is no antigen in the sample, no sandwich can be formed and hence no visible color signal can be seen in the third domain. This is a so-called non-competitive immunoassay or a sandwich assay where the amount of signal is directly proportional to the concentration of the analyte of interest in the sample.

Lateral-flow chromatographic immunoassay cassettes can also be adapted for competitive immunoassays. In a competitive immunoassay, the analyte of interest in the unknown sample competes for binding to an antibody with a labeled analyte. In a competitive assay, the labeled analyte is able to provide a known signal. In the assay, the amount of labeled analyte bound to the antibody is measured and any reduction in the known signal is attributed to the presence of the analyte in the sample. That is, in this method, the response will be inversely related to the concentration of analyte in the unknown. This is because the greater the response, the less antigen in the unknown was available to compete with the labeled antigen.

Lateral-flow chromatographic immunoassay cassettes may be adapted for assaying a number of different analyte types. For example, immunoassay cassettes have been adapted or may in the future be adapted for blood glucose testing, metabolic testing (e.g., thyroid stimulating hormone), blood gas and electrolytes analysis, rapid coagulation testing, rapid cardiac markers diagnostics, drugs of abuse screening, urine testing, pregnancy testing, fecal occult blood analysis, food pathogen screening, complete blood count ("CBC"), hemoglobin diagnostics, infectious disease testing (e.g., a multi-analyte rapid diagnostic test for detecting malaria infection), cholesterol screening, hormone testing, cardiac pulmonary, gastroenterology, urology, renal, dermatology, neurology, pediatrics, surgical, public health, and veterinary and plant pathology testing, combinations thereof, and the like.

In addition to the foregoing, another embodiment of a lateral flow immunoassay cassette is described. Examples of such lateral flow immunoassay cassettes are shown at 200 in FIGS. 2A and 2B and at 300 in FIGS. 3A and 3B. In the lateral flow immunoassay cassettes 200 and 300, a test sample (i.e., a sample containing an unknown concentration of an analyte of interest) may be run in parallel with a calibration standard (i.e., a sample containing a known concentration of the analyte of interest). The response to the known concentration of the analyte of interest in the calibration standard on the lateral flow immunoassay device may be used to generate a calibration curve that can be used to quantify the amount of the analyte of interest in the test sample.

Such an arrangement may provide superior results. For example, the test and calibrations strips of such cassettes may be manufactured side-by-side under substantially equal temperature and humidity conditions. As a result, it is generally the case that the test and calibrations strips each have the same amount on antibody immobilized thereon and that the antibody on each will react substantially the same. Also, because the test and calibration assays are run in parallel, the test and calibration results are generally unaffected by factors like temperature and humidity. This is generally not the case if the test and calibration assays are run at separate times on strips that may have been manufactured at different times. Likewise, because the test and calibration assays are run in parallel, the cassettes and a reader device, if used, are calibrated for each assay run on each cassette, which is believed to provide more reliable quantitative results.

The lateral flow immunoassay cassette 200 illustrated in FIGS. 2A and 2B includes a base 214 that includes a test strip 201a and a calibration strip 201b. The test strip 201a includes a sample application zone 202a with a sample collection pad 216a, a conjugate pad 204a, a test assay strip 206a (e.g., a nitrocellulose ("NC") membrane), and an absorbent pad 212. Likewise, the calibration strip 201b includes a sample application zone 202b with a sample collection pad 216b, a conjugate pad 204b, a calibration strip 206b, and the absorbent pad 212. Each of the test assay strip 206a and the calibration strip 206b include at least one capture binding moiety 208a and 208b (e.g., an antibody, a nucleic acid, or the like) that can specifically interact with and capture the analyte of interest for detection. In one embodiment, the sample pad 212 may include flow indicator lines 210a and 210b (e.g., a water soluble dye) that indicate whether or not sample has successfully diffused through the test strip 201a and the calibration strip 201b.

In the illustrated embodiment, the test 201a and calibration strips 201b are run in opposite directions (i.e., both the test sample and calibration standard flow toward absorbent pad at the center of the cassette). In other embodiments, the test and calibration strips may be arranged such that the test sample and calibration standard flow parallel to one another. Such an embodiment may, for example, include a divider arranged between the test assay strip and the calibration assay strip.

Figure 3A:
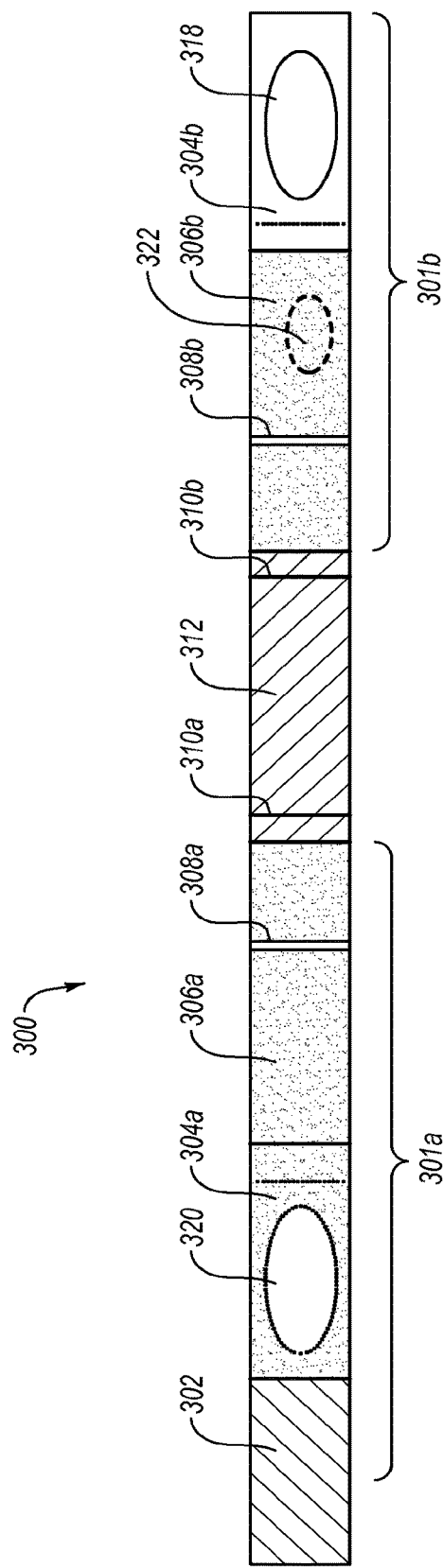
FIGS. 3A and 3B illustrates a lateral flow immunoassay device according to another embodiment of the present invention.
Figure 3B:
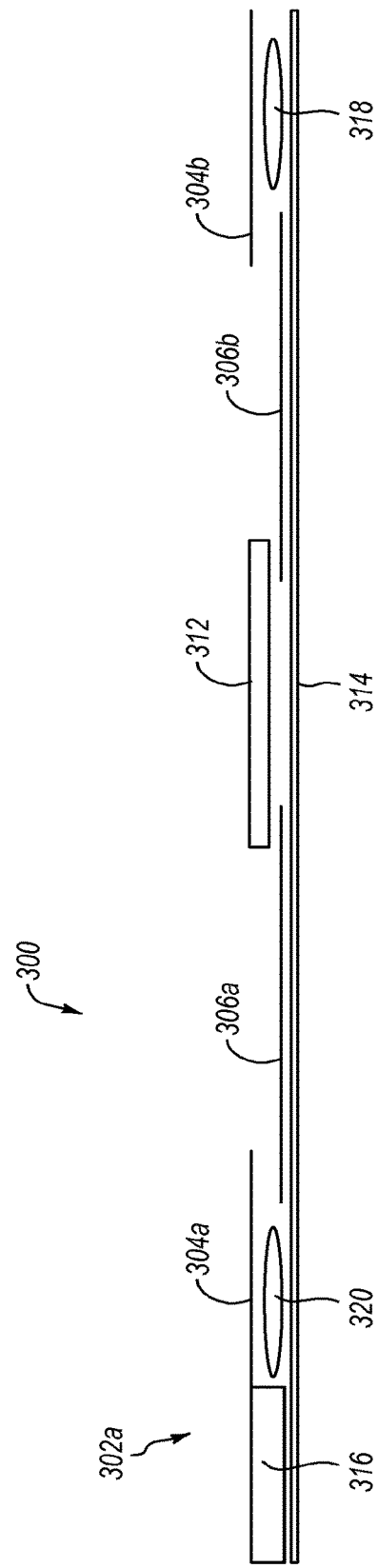

The lateral flow immunoassay cassette 300 illustrated in FIGS. 3A and 3B is similar to the cassette 200 of FIGS. 2A and 2B. The lateral flow immunoassay cassette 300 includes a base 314 that includes a test strip 301a and a calibration strip 301b. The test strip 301a includes a sample application zone 302a with a sample collection pad 316, a conjugate pad 304a, a test assay strip 306a (e.g., a nitrocellulose ("NC") membrane), and an absorbent pad 312. In addition, the test strip 301a includes includes a sachet 320 (e.g., a blister pack) of buffer that can be used to chase (i.e., wash) a test sample through the conjugate pad 304a and the assay strip 306a toward the absorbent pad 312.

In contrast to the cassette 200 of FIGS. 2A and 2B, the cassette 300 omits a calibration standard application zone and instead includes a standard solution sachet 318 that contains a known volume of a solution that contains a known amount of at least one analyte of interest. When the a standard solution sachet 318 is pierced at the time of use, the solution wicks through the conjugate pad 304b and the calibration strip 306b toward the absorbent pad 312. Each of the test assay strip 306a and the calibration strip 306b include at least one capture binding moiety 308a and 308b (e.g., an antibody, a nucleic acid, or the like) that can specifically interact with and capture the analyte of interest for detection. The characteristics of the standard solution sachet 318 can be used to test for quantitative delivery of the calibration standard onto the calibration strip 306b and to test the response of the capture binding moiety 308b to the analyte of interest. In one embodiment, the sample pad 312 may include flow indicator lines 310a and 310b (e.g., a water soluble dye) that indicate whether or not sample has successfully diffused through the test strip 301a and the calibration strip 301b.

In one embodiment, the sample pad 216a, 216b, or 316 may be configured to absorb and dispense a predetermined amount of a fluid from the fluid that is applied thereto. That is, the sample pad 216a, 216b, or 316 may be fabricated from an absorbent-type material that may saturated with fluid and then when, for example, the sample pad 216a, 216b, or 316 is compresses or squeezed, the sample pad 216a, 216b, or 316 can dispense a predetermined amount of a fluid therefrom. In one embodiment, the sample pad 216a, 216b, or 316 may be made of cellulose, glass fiber or other material where the fluid sample is applied to the lateral flow device and, if necessary modifies it to improve the results of the assay. This might be by modifying pH, filtering out solid components, separating whole blood constituents, adsorbing out unwanted antibodies or some other test specific variable.

For some applications, the sample pad 216a, 216b, or 316 may be pretreated by dipping it into a specific buffer containing a mix of a solution comprised of soluble proteins, surfactants/detergents, and other polymers. These may allow for a steady flow and prevent nonspecific binding of sample components to the pad 216a, 216b, or 316.

In some embodiments, the sample may be added to the sample pad 216a, 216b, or 316 by collecting a liquid sample (e.g., blood, urine, or saliva) and adding a selected volume of the sample to the sample pad. In other embodiment, the sample may be added to the sample pad 216a, 216b, or 316 by soaking the pad with a fluid sample. For example, the sample pad 216a, 216b, or 316 may be soaked with saliva by inserting the sample collection pad 216a, 216b, or 316 end of the device 200 or 300 into the mouth to collect a saliva sample.

In one embodiment, the conjugate pad 204a, 204b, 304a, 304b is made of a non-absorbent material such as fiberglass pad, polyester, rayon or a similar material. The conjugate pad 204a, 204b, 304a, 304b is typically fabricated from a synthetic material (at least when using a gold conjugate) to ensure the efficient release of its contents.

As its name implies, the assay's detection conjugate (e.g., colloidal gold) is dried down and held in place in the conjugate pad 204a, 204b, 304a, 304b until a liquid test sample is applied to the sample pad. The liquid from the sample, by capillary action moves into the conjugate pad 204a, 204b, 304a, 304b, re-hydrates the dry conjugate and allows the mixing of the sample with the conjugate. The complex of conjugate and analyte then moves into and up the assay strip 206a, 206b, 306a, 306b. Pretreatment of the conjugate pad 204a, 204b, 304a, 304b helps to ensure the conjugate releases at the proper rate and enhances its stability. The pretreatment is performed in the same way as with the sample pad 216a, 216b, or 316.

In one embodiment, the at least one capture binding moiety 208a, 208b, 308a, 308b may be added to the test or calibration strips with a dispenser that gently slides a soft capillary tube across the membrane. A dispenser pump releases a constant volume of the reagents down the length of the membrane. This system is simple, easy to use, and low cost. They can be somewhat cumbersome in large scale manufacturing and many systems require a technician to constantly feed the nitrocellulose cards and to monitor reagent levels as well as the quality of the test and control lines.

An alternative method of applying the at least one capture binding moiety 208a, 208b, 308a, 308b includes a non-contact aerosol system. These sprayers dispense solutions in controlled ultrafine, ultra-small volume aerosols. These devices project very fine droplets of reagent onto the membrane and overlap the drops to create a continuous line. Spraying offers much more control of the reagent application, but it also adds capital expense and increases the complexity of strip manufacturing. These devices are more appropriate in very large scale manufacturing or when a reader with tight tolerances will be used to analyze the lateral flow test strips.

In the foregoing, addition of one line of the at least one capture binding moiety 208a, 208b, 308a, 308b onto each of the test or calibration strips is discussed. However, one will appreciate that a cassette 200 or 300 may include multiple test and control lines that may each be configured to interact with a different analyte of interest.

Figure 4B:
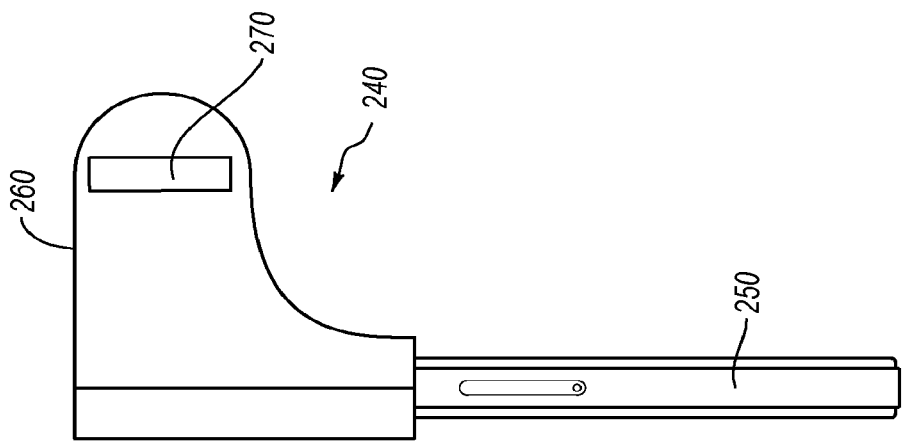
FIG. 4B illustrates a side view of the diagnostic test system of FIG. 4A.
Figure 4A:
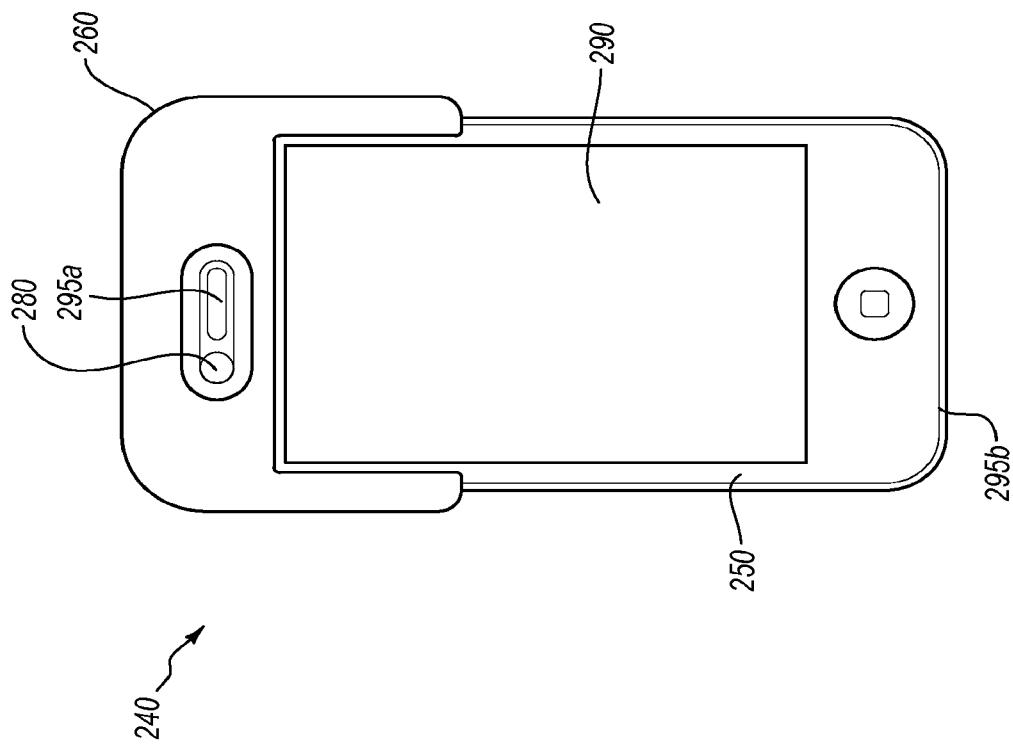
FIG. 4A illustrates a plan view of a diagnostic test system that includes a digital camera device and a testing apparatus configured to couple the lateral-flow chromatographic immunoassay cassette to the digital camera device.

Referring now to FIGS. 4A and 4B, plan and side views of a diagnostic test system 240 are illustrated. In one embodiment, the diagnostic test system 240 may include a handheld device 250 and a testing apparatus 260.

In the illustrated embodiment, the handheld device 250 is an iPhone. However, the handheld 250 device can be essentially any cell phone device, digital camera device, or a similar device that has an onboard camera/image capture function, data collection and analysis capabilities, data and results display capabilities, and, preferably, the ability to communicate with one or more remote computer or cell-phone networks for data upload, querying a data analysis algorithm, querying a decision support algorithm, and the like. In the illustrated embodiment, the handheld device 250 includes a front-directed camera 280, a back-directed camera (not shown) that is directed into the testing apparatus, a display screen 290, and audio input and output ports 295a and 295b. The display screen 290 can be used for display of data and results. In addition, the display screen 290 may include touchscreen capabilities that can be used for input of data or commands. Additionally the front-directed camera can be used for imaging QR and bar code information identifying the test to be performed and providing lot number, expiration date, and control values as well as other parameters as needed for test identification, calibration, results interpretation, and data reporting.

In one embodiment, the testing apparatus 260 is designed to be securely coupled to the handheld device 250. For example, the testing apparatus 260 may be designed to fit a specific class or brand of handheld devices. The testing apparatus includes a cassette port 270 that is designed to allow an assay device, such as a lateral flow immunoassay cassette 105 (see FIG. 1), to be inserted into the testing apparatus 260. Additionally, an interior portion of the testing apparatus 260 may be painted with a flat black color so as to avoid extraneous and reflected light. In addition, the testing apparatus 260 includes a number of internal components (e.g., i/o ports, power ports, light source(s), lens(es), light conducting media, etc.) that are designed to transform the handheld device 250 into a device that can be used to collect and analyze data produced by an assay device, such as the lateral flow immunoassay cassette 105 (see FIG. 1).

While the testing apparatus 260, is shown fitted to the handheld device 250, one will appreciate that they testing apparatus can be configured as a separate unit that includes its own light source, power supply, optics, data capture capabilities, and the like. In such an embodiment, the testing apparatus may be configured to collect assay data from an assay cassette and transfer it (e.g., by a wired or wireless connection, by Bluetooth™, or the like) to the handheld device for analysis and reporting.

Figure 5A:
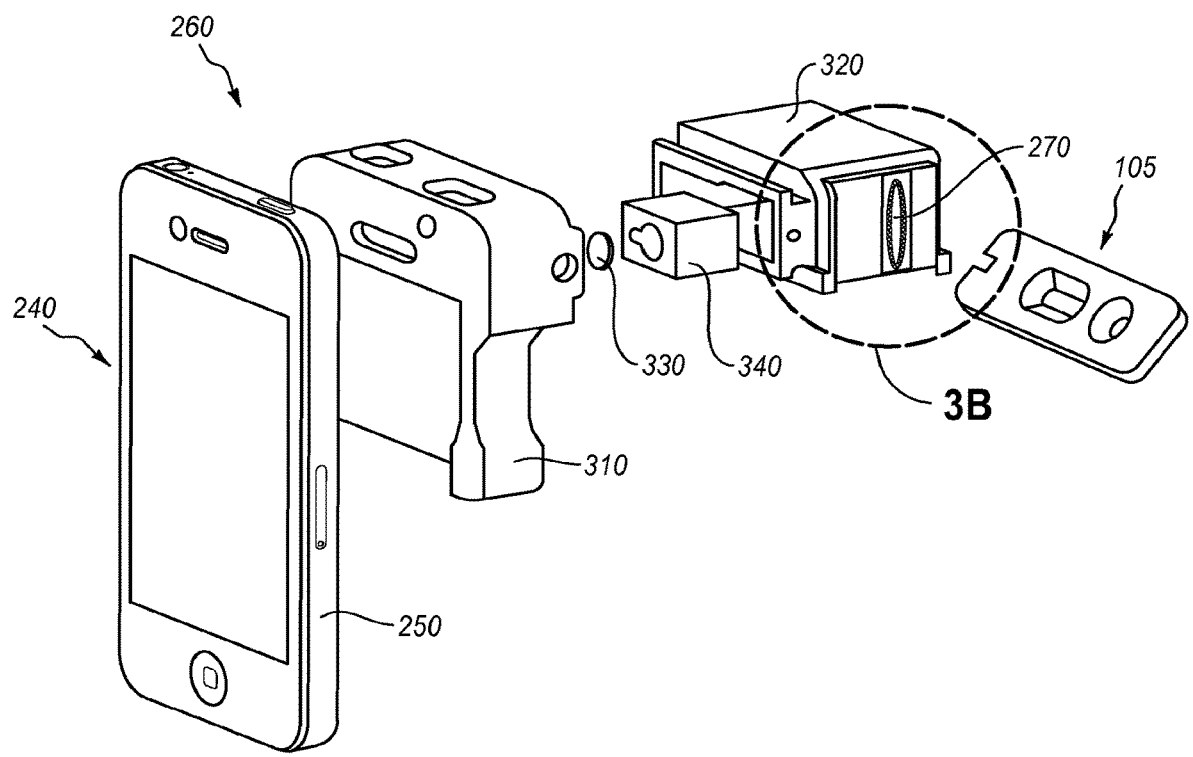
FIG. 5A illustrates an exploded view of the diagnostic testing system that is illustrated in FIGS. 4A and 4B.

Referring now to FIG. 5A, FIG. 5A illustrates an exploded view of the diagnostic testing system 240 that is illustrated in FIGS. 4A and 4B. As can be seen in the exploded view, the testing apparatus 260 includes a main body housing 310 and an assay housing 320.

The main body housing 310 is primarily designed to mate cleanly with the handheld device 250. For example, the main body housing 310 may be shaped such that the handheld device 250 can be slid into the main body housing 310 such that the handheld device 250 clicks into or otherwise securely mates with the main body housing 310. The main body housing 310 may also include one or more gaskets, seals, and the like that allow the handheld device to form a secure and light-tight seal with the main body housing 310. Additional features of the main body housing 310 will be discussed below.

The assay housing 320 is fixedly coupled to the main body housing 310. In the illustrated embodiment, the assay housing 320 includes a cassette port 270 that is configured such that a lateral flow immunoassay cassette 105 can be inserted into the assay housing 320. In addition, the assay housing 320 in the in the illustrated embodiment includes a lens that is interposed between the handheld device's 250 back-directed camera (not shown) and the lateral flow immunoassay cassette 105. Likewise, an optical fiber device or light pipe 340 that is capable of transmitting light either to the lateral flow immunoassay cassette 105 from the hand held device's 250 light source (not shown), from the lateral flow immunoassay cassette 105 to the hand held device's 250 back-directed camera (not shown), or both.

While the hand held device's 250 light source (not shown) can be used to illuminate the lateral flow immunoassay cassette 105, the diagnostic testing system 240 may also include one or more additional light sources that can be housed in either the assay housing 320 or the main body housing 310. Suitable examples of light sources can include, but are not limited to a camera flash, an autofocus illuminator on a camera, an LED light, an incandescent lamp, or a gas-discharge lamp. For example, the light source can come from micro-LED lamps that are included in the assay housing 320. The micro-LEDs can be selected to emit certain wavelengths that are adapted for one or more assay conditions. The micro-LEDs can be powered by drawing electrical power from the battery of the handheld device 250. In addition, either the assay housing 320 or the main body housing 310 may be configured such that ambient light or sunlight can be used to illuminate the lateral flow immunoassay cassette 105.

In one embodiment, at least one wavelength filter may be interposed between the light source and the lateral-flow chromatographic immunoassay cassette 105. For example, if the assay is a fluorescent assay, then the wavelength filter may be used to yield a specific wavelength of light from the light source to excite fluorescent emission from the assay system. Likewise, certain colored dyes may yield a better signal when excited by selected wavelengths of light.

In one embodiment, the lens 330 (e.g., a collimating lens) may be used for focusing the light source on the lateral-flow chromatographic immunoassay cassette 105. For example, the lens 330 may be used to increase the amount of incident light impinging on the lateral-flow chromatographic immunoassay cassette 105. For instance, the purpose of the lens 330 may be to bring the focal point of the camera of the handheld device 250 (which is limited to about 6 inches or more) to less than 2 centimeters. This allows for a smaller overall package and produces a finer image that prevents the use of convoluting a blurry picture using Fourier transforms in order to produce a usable data that can be analyzed. Furthermore, with a multi-analyte detection assay (e.g., two calibration standard lines and a test sample line), the finer image will prevent overlap of the target lines to improve sensitivity and accuracy. In another example, a focusing apparatus may be used to focus ambient light or sunlight on the analysis zone of the lateral-flow chromatographic immunoassay cassette 105.

In some embodiments, the assay cover 320 may include a device that can allow the angle of the lateral-flow chromatographic immunoassay cassette 105 to be adjusted relative to the handheld device 250 and a light source (not shown). By selectively modifying these angles, the lower detection limit of the assay can be extended, the signal to noise ratio can be improved, etc. In one embodiment, the device can be adjusted manually in order to choose an angle that optimizes detection limit, signal to noise, and the like. In another embodiment, the device can be coupled to a mechanical means, such as a servo motor or a gel-damped spring device that can allow the device to automatically sample a number of angles while the handheld device 250 collects data from the lateral-flow chromatographic immunoassay cassette 105.

Figure 5B:
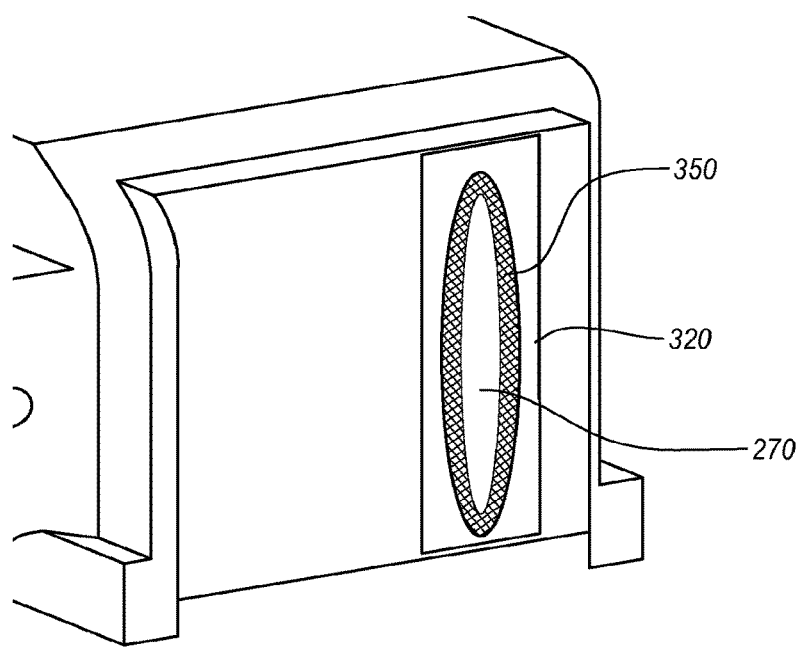
FIG. 5B illustrates a view of a component of the diagnostic test system shown in FIG. 5A, wherein the component includes a light sealing feature.

Referring now to FIG. 5B, the assay housing 320 and the cassette port 270 are illustrated in greater detail. In the embodiment illustrated in FIG. 3B, the cassette port 270 of the assay housing 320 includes a sealing gasket 350 disposed around the cassette port 270 that can seal the cassette port 270 when an assay cassette 105 is inserted therein so that ambient light does not leak into the housing 260. For example, if ambient light leaks into the housing 260, it could skew results. In addition, the cassette port 270 may include a spring-loaded flap (not shown) or similar means that can seal ambient light out of the housing 260 even when no cassette 105 is inserted into the cassette port 270.

Figure 6:
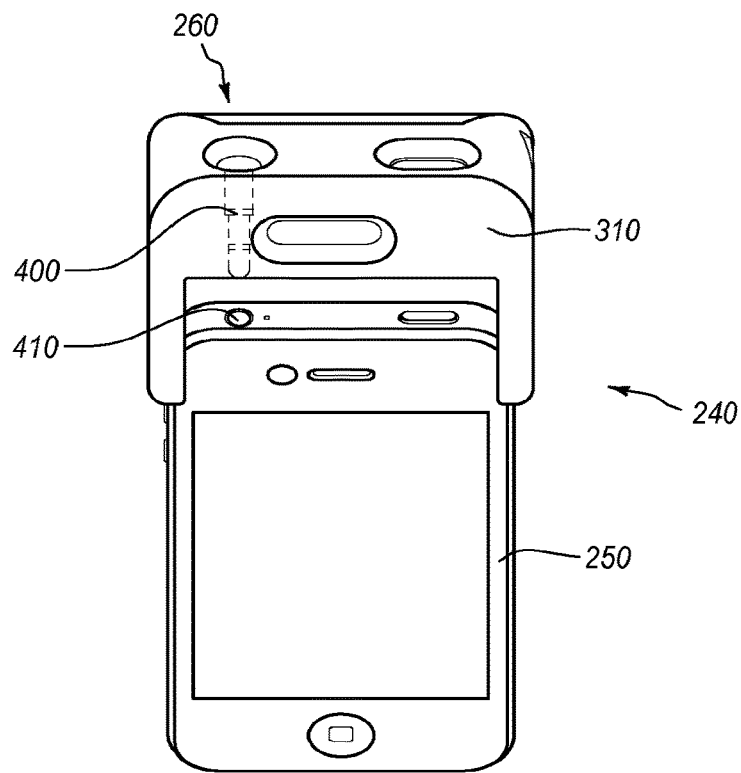
FIG. 6 illustrates a view of a diagnostic test system that includes an indexing feature for aligning the digital camera device and the testing apparatus.
Figure 7A:
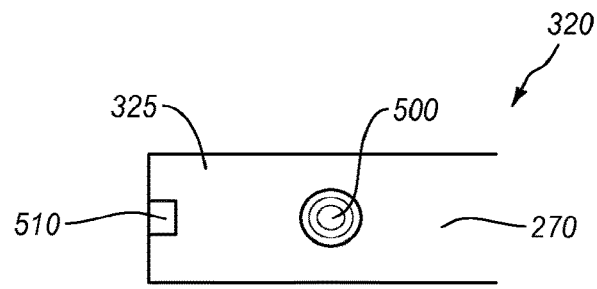
FIG. 7A is a cut-away view of a testing apparatus of a diagnostic test system illustrating a target device configured for normalizing and/or calibrating the light source and the detector of the diagnostic test system.
Figure 7B:
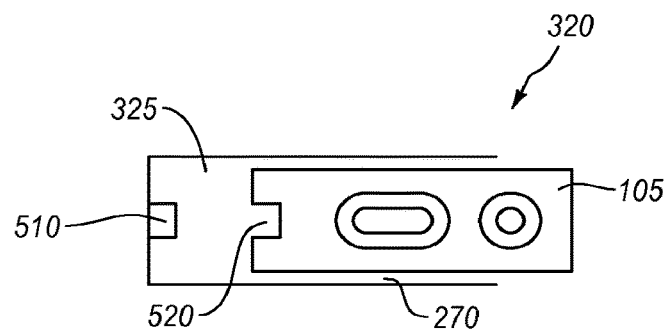
FIG. 7B is a cut-away view of a testing apparatus of a diagnostic test system illustrating a mechanical interlock feature configured to interlock with a corresponding second mechanical interlock feature on a lateral-flow chromatographic assay cassette.

Referring now to FIGS. 6, 7A, and 7B, additional features of the housing 260 are illustrated.

Referring to FIG. 6, an example of an indexing feature that can reliably align the housing 260 relative to the handheld device 250 is illustrated. In the illustrated embodiment, the indexing feature may include a headphone jack 410 that is integrated into the housing body 310. When the handheld device 250 is inserted into the housing body 310, the headphone jack 400 is positioned such that it can be inserted into the headphone port 410 of the handheld device 250. It will be understood by persons having ordinary skill in the art that headphone jack 400 is but one example of an indexing feature and that additional indexing features can be employed without departing from the spirit of this discussion.

In addition to aligning the housing body 310 relative to the handheld device 250, the headphone jack 400 can be used to draw electrical power from the handheld device 250 in order to power components (e.g., one or more illumination devices) that are positioned in the housing 260. Likewise, the headphone jack 400 can be used for data transfer between the handheld device 250 and components in the housing 260.

Referring now to FIG. 7A, a target device 500 is illustrated. The target device 500 can be used to normalize/calibrate the response of at least one of the camera or the light source of the handheld device. In one embodiment, the target device may located on an interior surface 325 of the assay housing 320 in close proximity to the cassette port 270 in an area that is can be illuminated by a light source that will be employed for illumination of an assay cassette and viewable by a camera of a handheld device that is going to be used to capture data from the cassette. For example, the target device may have a known color and/or color intensity that can give a known response for calibrating the light source and the camera. In addition, the target device 500 can be used to ensure that the light source and the camera are directed at the proper point when the handheld device in inserted into the housing.

Referring now to FIGS. 7A and 7B, the assay housing 320 may further include a mechanical interlocking feature 510 that is positioned and configured to mate with a mechanical interlocking feature 520 on the assay cassette. For example, the mechanical interlocking features 510 and 520 may include tab and cut-out features that are designed to fit together. Such mechanical interlocking features 510 and 520 may be used to ensure that the cassette 105 is inserted in to the assay housing 320 in the proper orientation. In addition, such mechanical interlocking features 510 and 520 may be coupled to a disabling feature that can shut down the device if an incompatible cassette is inserted into the housing 320 or if the cassette is inserted in the wrong orientation. This can, for example, be an important safety feature because it prevents the device from reading the wrong portion of the cassette and giving an erroneous reading as a result.

II. Methods for Detecting at Least One Analyte of Interest in a Sample

In one embodiment, a method for detecting at least one analyte of interest in a sample is disclosed. The method includes providing a lateral-flow chromatographic assay cassette and providing a testing device that is capable of interfacing with the lateral-flow chromatographic assay cassette.

In an embodiment, the lateral-flow chromatographic assay cassette may include a capture ligand capable of capturing and localizing at least one analyte of interest in a sample on an analysis surface of the lateral-flow chromatographic assay cassette, at least one reporter configured for interacting with at least one of the analyte of interest or the capture ligand, and at least a first calibration standard and a second calibration standard configured to provide at least a two-point calibration curve. In another embodiment, a lateral-flow chromatographic assay cassette may include an absorbent test strip for analyzing an analyte of interest in an experimental sample and an absorbent calibration strip for running at least one calibration standard positioned in proximity to the absorbent test strip as described in greater detail elsewhere herein.

Figure 8:
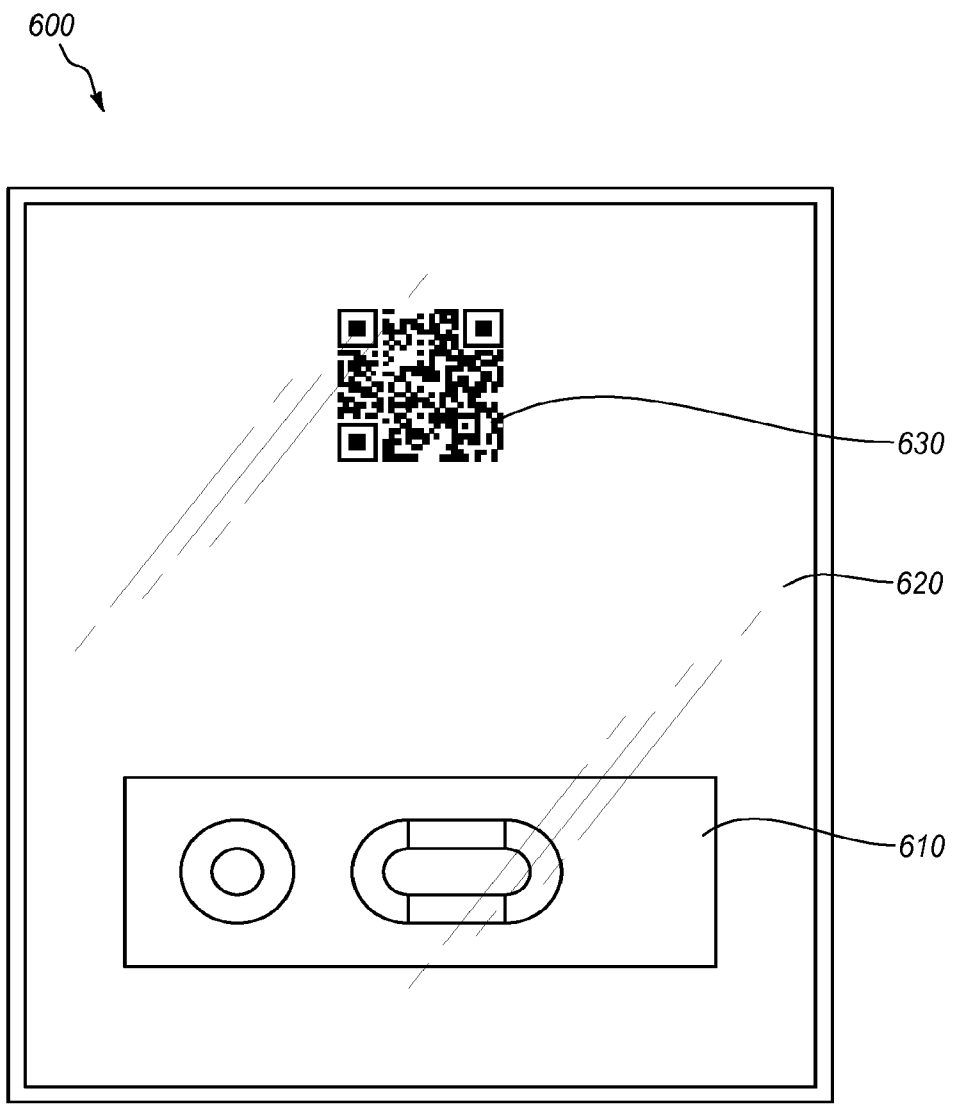
FIG. 8 illustrates a lateral-flow chromatographic assay cassette packaging system that includes a tracking feature readable by the handheld device.

In one embodiment, the lateral-flow chromatographic assay cassette may be packaged in a packaging system 600, as illustrated in FIG. 8. The packaging system 600 includes a sealed package (e.g., a plastic-, foil-, or paper-based package) that can be used for containing, storing, or transporting the lateral-flow chromatographic assay cassette 610 in a clean and preferably sterile environment. A QR code decal or sticker with relevant cassette information could be applied or printed to the outside of each foil pouch or canister.

In addition, the packaging system 600 includes a tracking code 630. In the illustrated embodiment, the tracking code 630 is a QR code, which is a two-dimensional bar code. Two-dimensional bar codes, like QR codes, can be used to store far more information that can be stored in a conventional bar code. For example, a QR code can be used to store up ~4300 alphanumeric characters (i.e., 0-9, A-Z, space, $, %, *, +, −, ., /, :, etc.). In one embodiment, the tracking code 630 can be read by the diagnostic testing system prior to initiating a test. The tracking code may be used to store information that is relevant to the test in a format that can be read by the device. For example, the tracking code 630 can be used for recording and then transmitting to the test system the values for the calibration standards used on the lateral-flow chromatographic assay cassette 610, manufacturer, date of manufacture, lot number for the lateral-flow chromatographic assay cassette 610, manufacturer, date of manufacture, and sample/results tracking.

The testing device may include a testing apparatus that is configured to couple the lateral-flow chromatographic assay cassette to the handheld device in proximity to a light source, the light source being capable of transmitting at least one wavelength of light configured to yield a detectable signal from the reporter(s) (e.g., at least one reporter configured for interacting with at least one of the analyte of interest in a test sample and/or a calibration sample, the first calibration standard, and the second calibration standard), and a detector is positioned to capture the detectable signal from the reporter(s).

The method may further include applying a liquid sample that includes at least one analyte of interest to the lateral-flow chromatographic assay cassette. In some embodiments, applying a liquid sample to the cassette may include applying separate test and calibration samples to separate test and calibration strips. The method may further include inserting the lateral-flow chromatographic assay cassette into the testing device, illuminating the lateral-flow chromatographic assay cassette with the light source of the testing device in order to yield a detectable signal from the reporter(s), and querying an interpretive algorithm for (i) calculating the calibration curve and then (ii) converting the detectable signal from the first reporter to a numerical value related to the presence or amount of the at least one analyte present in a sample.

In one embodiment, the calibration curve may be calculated based on values from interaction of a first calibration standard and a second calibration standard with calibration standard lines on the cassette. See, e.g., calibration standards lines 150*a* and 150*b* of FIG. 1. In another embodiment, the calibration curve may be calculated based on (1) observing a blank region of the absorbent calibration strip, and (2) generating a two point calibration curve that includes a value for the interaction of the analyte of interest from the liquid calibration standard with the ligand immobilized on the absorbent calibration strip and a value for the blank region of the absorbent calibration strip. An example of the blank region on a calibration strip 206*b* and 306 *b* is illustrated at 222 and 322 in FIGS. 2A and 3A. Because the calibration strip may not be pure white, the strip may produce a background signal that needs to be subtracted to get a true value for the signal from the test and calibration lines. Moreover, instead of assuming a zero value, observing the background signal in the blank region allows the calculation of a true two-point calibration curve, which is more accurate.

In one embodiment, the method may further include providing means for dispensing a known amount of liquid from a sample pad of the assay cassette. Such means may include, without limitation, rollers, presses, rollers or presses that include a stop that determines how much liquid can be squeezed from the samples pad, spring loaded devices that automatically press down on the sample pad to dispense a predetermined amount of liquid, and the like. In one embodiment, the testing device may include means for dispensing a known amount of liquid from the sample pad. For example, the testing device may include a port for inserting the lateral-flow chromatographic assay cassette into the testing device. Such a port may, for example, include a roller or a similar means that rolls over the sample pad and dispenses a selected amount of liquid therefrom when the cassette is inserted into the testing device.

In one embodiment, a single immunoassay device may contain multiple types of different capture moieties (e.g., antibodies) each conjugated with different dyes (e.g., quantum dots) and/or multiple capture bands each immobilized with different capture moieties. A single light source (e.g., an ultraviolet light) illuminates all dyes (e.g., quantum dots) simultaneously, and the detector device (e.g., a digital camera) captures the emitted signals from multiple bands simultaneously.

In one embodiment, analytes of interest assayed on the lateral flow immunoassay cassettes described herein may be detected and quantified by elastic light scattering. The amount of light scattered from a selected region of a lateral flow immunoassay cassette (e.g., a capture band) is highly sensitive to the amount of material in a region illuminated by an incident light. In general, elastic light scattering, coupled with angle optimization, may be as much as 100 times more sensitive than comparable reflectance or fluorescence analysis. Other excitation/detection methods may include surface plasmon detection; Rayleigh scattering, reflectance, diffuse scattering, electrochemical detection, conductivity, fluorescence, magnetic, enzymatic, transmission, absorption, acoustic detection, any other method which is based upon Beer's law, kinetic analysis (e.g., change in signal strength over time), and the like.

In one embodiment, a light source may be positioned at a certain angle to the lateral flow assay cassette and the detector (e.g., a detection fiber or a cell phone camera) or fiber (eventually the cellphone camera CCD). In one embodiment, the reporter(s) may be queried by taking a reading from each reporter and calculating the intensity of the scattered light. Signal intensity (i.e., the amount of scattered light that is detected) decreases as the concentration of the analyte of interest increases.

In an embodiment that includes a cell phone camera or the like, the camera's CCD will take an image. In one embodiment, the image may be taken with a red distance filter. In the image, the calibration standard lines and the test lines will be present. The digital image will then undergo digital image processing with a selected digital processing algorithm to produce a representative image of the color bands for the calibration standard lines and test simultaneously. For example, a digital processing algorithm may (1) identify the areas of interest (e.g., the test line and the at least two calibration standard lines) in the image taken of the lateral flow immunoassay cassette, (2) calculate an RGB value for each pixel in the image, (3) convert RGB format to xyz format, (4) convert xyz format to Lab color format, (5) assign a numerical value to each of the areas of interest (e.g., the test line and the at least two calibration standard lines), (6) calculate a calibration curve based on the numerical values obtained from the first and second calibration standard lines values, and (7) convert the numerical value for the test line into a concentration value for the analyte of interest in the sample.

In addition, internal controls, such as but not limited to, a control line (e.g., a fluorescent marker) to potentially eliminate or reduce variations in the final signal from manufacturing tolerances of the lateral flow assay cassette may be used to increase the robustness and reliability of the analysis. Additionally, analysis of the white portion of the lateral flow assay cassette may be used as an additional negative control to further improve reproducibility.

Figure 9:
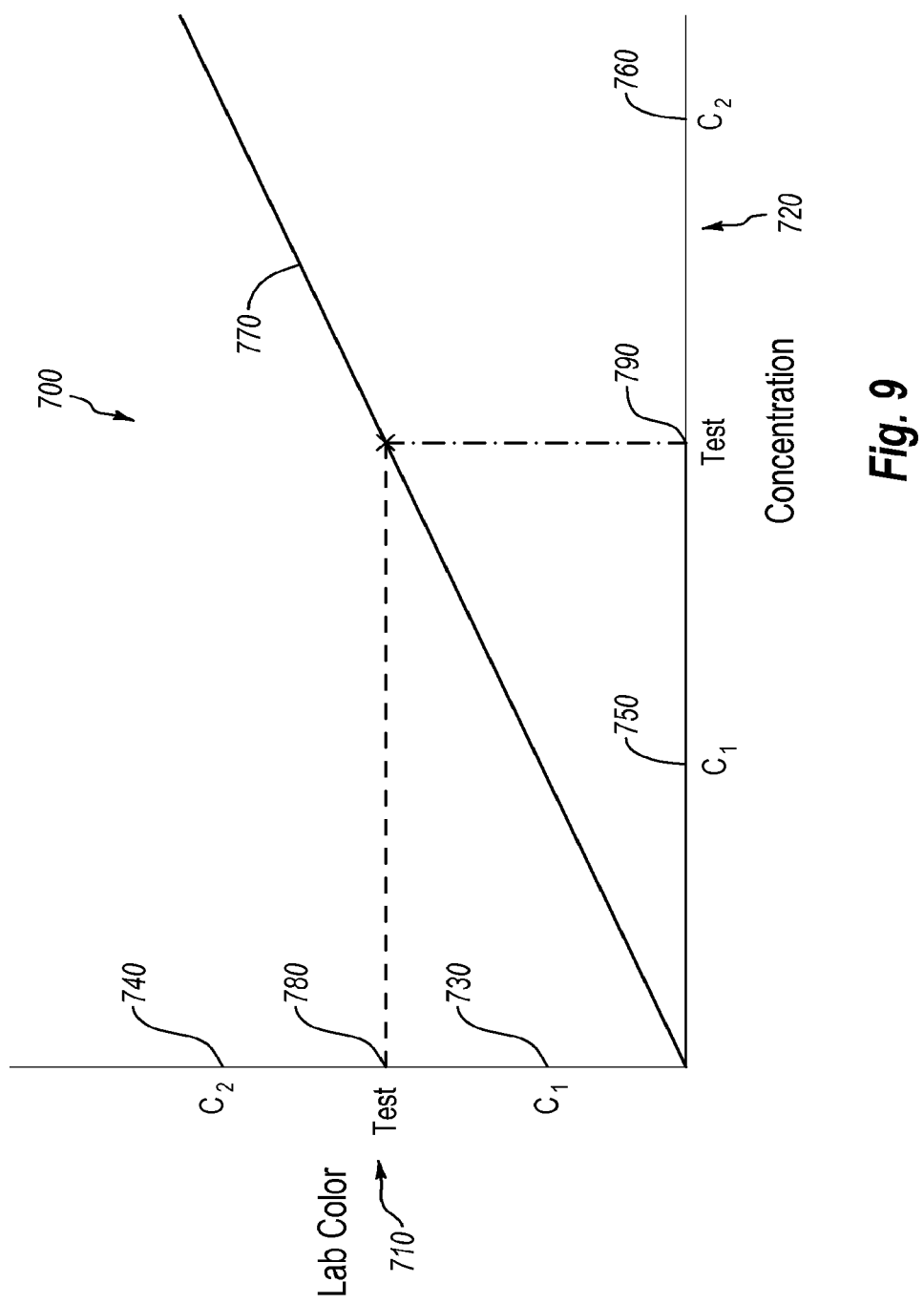
FIG. 9 illustrates a two point calibration curve according to one embodiment of the present disclosure.

The digital processing algorithm is able to convert the numerical value for the test line into a concentration value because the at least two calibration standard lines are selected to provide numerical values that are proportional to non-zero concentration amounts for the analyte of interest. This relationship is clarified by reference to FIG. 9, which shows a graph 700 with Lab value on the Y-axis and concentration on the X-axis. The first and second calibration standards have a known response that relates to known and, preferably, non-zero concentration values for the analyte of interest. Lab values for each of the first and second calibration standards 730 and 740 can be related to a concentration for each 750 and 760 by a simple relationship. By relating observed Lab color values to concentration values 750 and 760, a calibration curve 770 can be generated that can be used to calculate the concentration 790 of the analyte of interest in the sample based on the observed Lab color 780. One will of course appreciate that the calibration curve 770 can also be described by a mathematical formula and that the analysis algorithm may not actually generate a calibration curve, per se.

In one embodiment, the method may further include mixing the liquid sample with a dye conjugate prior to applying the sample to the lateral-flow chromatographic immunoassay cassette. In one embodiment, the dye conjugate is configured to interact with at least one of the analyte of interest or the ligand to provide a visual readout related to the presence or concentration of the analyte of interest in the sample. In one embodiment, the sample includes at least one control substance and at least one analyte of interest.

In one embodiment, the observation of the interaction of the at least one analyte of interest with the at least one ligand immobilized on the lateral-flow chromatographic immunoassay cassette may be timed by observing the appearance of at least one control substance. For example, a thyroid stimulating hormone ("TSH") assay may be read ~10 minutes after a diluent is applied. By monitoring the position of the wave front or the appearance of the control line, it may be possible to eliminate the need to manually time the test. Likewise, by observing the timing of the appearance of a control, the most favorable time for reading the assay can be identified. These could include monitoring the movement of the mobile phase, monitoring the movement of the control substance, timing the movement of the mobile phase, taking sequential images of the test result, detecting when buffer is added, detecting when liquid has traveled the length of the membrane, and combinations thereof.

In addition, testing device may include or may be configured to access an interpretive algorithm stored in a computer readable format and electronically coupled to the handheld device, wherein the interpretive algorithm is configured to (i) calculate a calibration curve based on the first calibration standard and the second calibration standard and then (ii) convert the detectable signal from the first reporter to a numerical value related to the presence or amount of the at least one analyte present in a sample. The interpretive algorithm may be included in an on-board computing system of the handheld device or the interpretive algorithm may be stored remotely in a computer storage medium that is accessible by the handheld device.

In one embodiment, the interpretive algorithm queried in the above described method may include one or more computer storage media having stored thereon computer executable instructions that, when executed by one or more processors of the detector device, implement a method for interpreting the numerical value related to the presence or amount of the at least one analyte present in the sample. In one embodiment, the computer implemented method may include (1) receiving a user initiated request to convert the visual signal readout of the immunoassay apparatus to a numerical value, (2) in response to the request, an act of identifying at least one visual signal readout of the immunoassay apparatus, (3) capturing at least one digital signal from the at least one visual signal readout of the immunoassay apparatus, (4) converting the at least digital signal to at least one numerical, and (5) using the at least one numerical value to determine an amount or concentration of at least one analyte present in the sample. This numerical value can then be displayed on a screen located on the detector device and/or stored, interpreted, or sent to a database.

In one embodiment, the computer implemented method may further include at least one of: (1) communicating with an electronic medical records system via a wireless communication channel, (2) uploading the amount or concentration of the at least one analyte present in the sample to the electronic medical records system, or (3) querying a decision support algorithm, wherein the decision support algorithm uses the at least one numerical value to support a diagnosis of at least one condition in a subject and to suggest a course of treatment.

Figure 10:
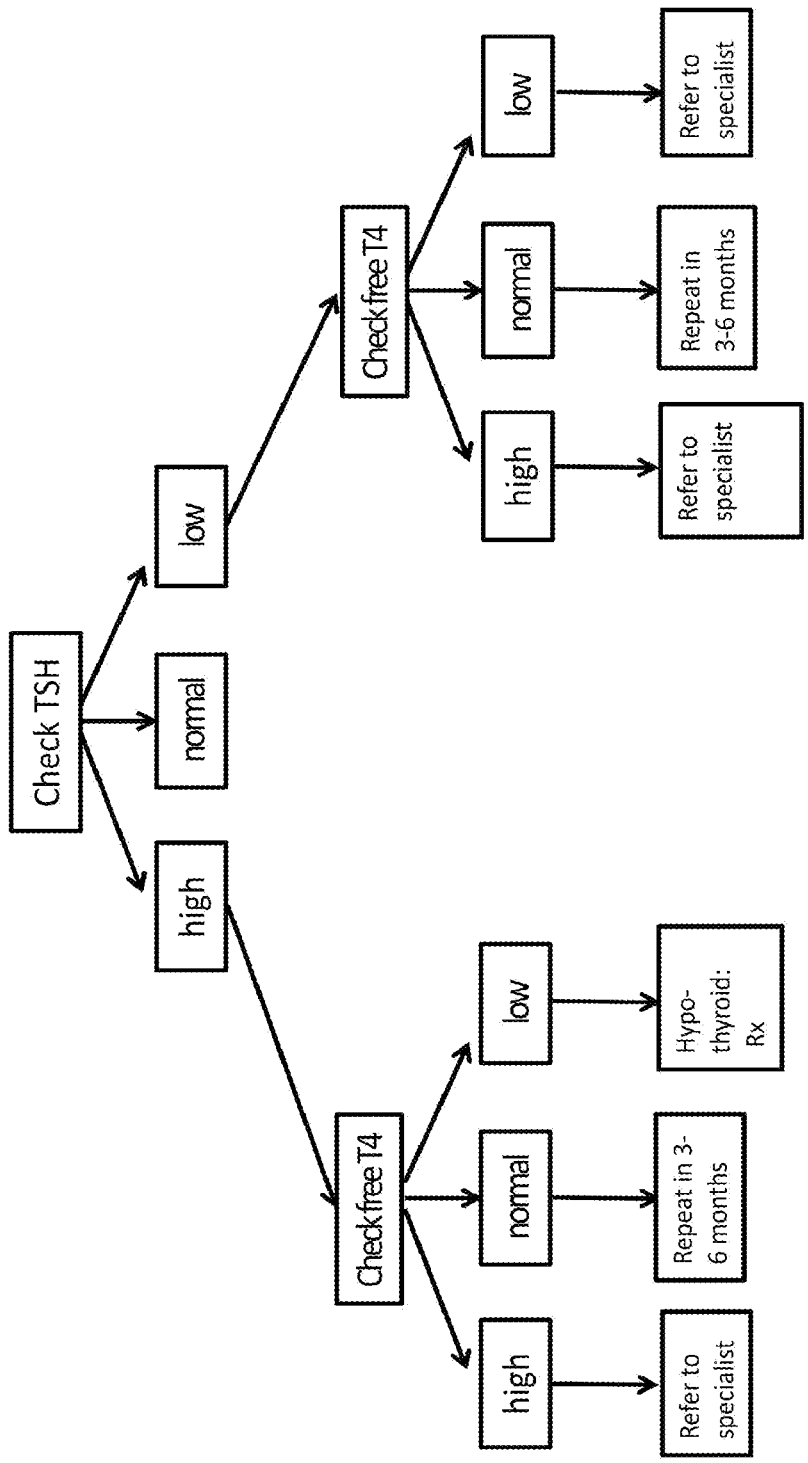
FIG. 10 is a decision tree schematically illustrating a decision support algorithm according to one embodiment of the present disclosure.

FIG. 10 schematically illustrates the decisions that may be made or actions that may be taken in an example decision support algorithm for a thyroid stimulating hormone (TSH) test. At the first branch point, if TSH is normal then no action is taken. If TSH is low, a clinician will be directed to check free thyroxine (T4). If free T4 is normal, the algorithm directs that the test should be repeated in 3-6 months; if free T4 is high or low, the algorithm directs that the patient should be referred to a specialist. If at the first branch point TSH is high, the clinician will be directed to check free T4. If free T4 is normal, the algorithm directs that the test should be repeated in 3-6 months; if free T4 is high, the patient should be referred to a specialist; and if free T4 is low, the algorithm directs that the patient should receive a treatment for hypothyroidism.

Embodiments of the present disclosure may comprise or utilize special purpose or general-purpose computing devices that include computer hardware, such as, for example, one or more processors and system memory, as discussed in greater detail below. Embodiments within the scope of the present invention also include physical and other computer-readable and recordable type media for carrying or storing computer-executable instructions and/or data structures. Such computer-readable recordable media can be any available media that can be accessed by a general purpose or special purpose computer system. Computer-readable media that store computer-executable instructions according to the invention are recordable-type storage media or other physical computer storage media (devices) that are distinguished from mere transitory carrier waves.

Computer-readable media that carry computer-executable instructions are transmission media. Thus, by way of example, and not limitation, embodiments of the invention can comprise at least two distinctly different kinds of computer-readable recordable media: computer storage media (devices) and transmission media.

Computer storage media (devices) includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer and which are recorded on one or more recordable type medium (device).

A "network" is defined as one or more data links or communication channels that enable the transport of electronic data between computer systems and/or modules and/or other electronic devices. When information is transferred or provided over a network or another communications connection or channel (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described herein. Rather, the described features and acts are disclosed as example forms of implementing the claims.

Those skilled in the art will appreciate that the invention may be practiced in network computing environments with many types of computer system configurations, including, personal computers, desktop computers, laptop/notebook computers, message processors, hand-held devices, multi-processor systems, microprocessor-based or programmable consumer electronics, network PCs, minicomputers, mainframe computers, tablets, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

In particular, one or more embodiments of the invention may be practiced with mobile consumer computing devices. Mobile consumer computing devices or more simply, mobile consumer devices, can be any of a broad range of computing devices designed or optimized for portability and for personal use. Mobile consumer devices can take a variety of forms, ranging from more traditional notebook and netbook computers to an emerging and rapidly growing market of handheld devices, including smart phones (e.g., the APPLE IPHONE, ANDROID phones, WINDOWS phones, SYMBIAN phones), tablet computers (e.g., the APPLE IPAD, ANDROID tablets), gaming devices (e.g., NINTENDO or PLAYSTATION portable gaming devices, the APPLE IPOD), multimedia devices (e.g., the APPLE IPOD), and combinations thereof. Many of these devices can enable rich user-interactivity by including combinations of output, input, and other sensory devices, such as touch- or pressure-sensitive displays (using capacitive or resistive technologies, for example), still and video cameras, Global Positioning System (GPS) receivers, magnetic compasses, gyroscopes, accelerometers, light sensors, proximity sensors, microphones, speakers, etc. These devices can also comprise a variety of communications devices, such as combinations of cellular modems (e.g., Global System for Mobile Communications (GSM), Code division multiple access (CDMA)), Wireless Fidelity (Wi-Fi) radios, Bluetooth radios, Near Field Communication (NFC) devices, etc. Many mobile consumer devices are expandable, such that a user can add new hardware and functionality not present during manufacture of the device. It will be appreciated that as the market for mobile consumer devices expands and develops, the functionality of these devices will also expand to utilize new and improved user-interaction devices and communications devices. The embodiments described herein are expansive and can also utilize any future developments in the field of mobile consumer devices.

EXAMPLE

The following Example describes an example of a test device that includes an iPhone and a test device coupled to the iPhone. The test device includes a slot for inserting a lateral flow assay cassette into the test device for reading and analysis by the iPhone.

There are a couple of challenges to imaging the measurement cassette. The first is to fill the iPhone's camera frame with as much of the detection strip as possible. This suggests a short distance between the camera and cassette. The second challenge is to evenly illuminate the detection strip to make image processing easier. This requirement suggests a longer distance.

Generally, even illumination is the more challenging requirement. In one embodiment, a light pipe or a similar device may be interposed between the illumination source (e.g., the iPhone's flash or another light source that is included in the test device). Light pipes are commercially available in various configurations, such as, but not limited to, cylinders and rectangles. The rectangle shape has been tested and been found to work better than the cylindrical configuration. The physical dimensions of the rectangular light pipe are in the following document online: http://www.lumex.com/specs/LPB-R0112051S.pdf, the entirety of which is incorporated herein by reference.

As described above with respect to the Figures, the test device may include an accessory lens that is disposed between the camera's lens and the lateral flow assay cassette. The lens currently being tested has a 20 mm focal length and 6 mm diameter. This lens was ordered from Thorlabs.com with physical dimensions selectable in several formats from: http://www.thorlabs.us/thorProduct.cfm?partNumber=LA1700-A, the PDF version is: http://www.thorlabs.us/Thorcat/4400/4414-E0W.pdf, the entireties of which are incorporated herein by reference. A 30 mm focal length should be a good value for filling the iPhone camera's frame and achieving even illumination of the detection strip. A focal length of 60 mm is also an interesting choice since the iPhone may not need a second lens. However, this may potentially limit sensitivity in the final measurement.

One will of course appreciate that either the light pipe or the lens may include one or more light filters that allow selective illumination of the detection strip and/or detection of selection wavelengths of light from the detections strip. Likewise, the test device may include one or more light sources that emit selected wavelengths of for illumination of the detection strip. Analysis of images or a detection strip configured for detection of TSH with colloidal gold with a properly configured light pipe show dips in reflectivity in all three color channels (red, blue, green). With a proper exposure, there is a greatest difference in the green channel, corresponding to the 580 nm peak in the reflectance spectrum. The green channel shows a difference for both controls and the measured sample. This suggests that it may be best to illuminate with a selected wavelength of light that gives the best signal-to-noise ratio for detection of signal from colloidal gold when observing in the vicinity of 580 nm.

In this Example, there are two large changes relative to the device shown and discussed with respect to the Figures. Both of these changes relate to the orientation of the cassette. In this version the cassette is flat relative to the iPhone body and the long axis of the cassette being aligned with the long axis of the iPhone body. The image sensor in the iPhone is asymmetrical with the long axis of the image sensor being aligned with the long axis of the phone body. Orienting the long axis of the detection strip with the long axis of the phone orients the detection strip with the axis of the image sensor that contains the most pixels. The distance between the camera body and the cassette should be the focal length of the lens, in the present configuration 30 mm.

The center of the measurement part of the cassette where the sample should be on axis with the center of the camera lens. The center of the light pipe should be in the center of the LED lamp and oriented with its long dimension along the long dimension of the camera. The cut out for the lens and the cut out for the light pipe will leave a fairly thin wall between the two cut outs. Placing a thin wall between the light pipe and the lens prevent the lens from being affected by light coming directly from the illumination source. In addition, it has been observed that the color of the body of the smartphone can affect illumination and the results obtained from an assay. For instance, it was observed that light from a white iPhone flash diffuses through the plastic case more than the light from a black iPhone flash. This confounding factor can, for example, be addressed by an algorithm correction or by placing a gasket or physical barrier around the flash to limit and control light diffusion.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for detecting at least one analyte of interest in a sample, the method comprising:
   providing a lateral-flow chromatographic assay cassette that includes: a capture ligand, at least one reporter substance for visualizing the interaction of the analyte of interest and the capture ligand, and means for providing an at least a two-point calibration curve for quantification of the at least one analyte of interest;

providing a handheld computing device selected from the group consisting of a handheld digital camera device, a cellular phone, a smart phone, and a table computer;

providing a testing apparatus configured to be coupled to the handheld computing device and configured to position the lateral-flow chromatographic assay cassette in proximity to a detector and a light source to control focal length from the detector to the lateral-flow chromatographic assay cassette and to control illumination of the lateral-flow chromatographic assay cassette by the light source, wherein the testing apparatus comprises an assay cover including a manual or electromechanical device configured to allow the angle of the lateral flow assay cassette to be adjusted relative to the light source to sample a number of angles while the handheld computing device collects data to determine the optimum angle for detection;

the light source being capable of transmitting at least one wavelength of light configured to yield a detectable signal from the at least one reporter; and a detector is positioned to capture the detectable signal from the at least one reporter;

applying a liquid sample to the lateral-flow chromatographic assay cassette, wherein the sample includes at least one analyte of interest;

inserting the lateral-flow chromatographic assay cassette into the testing apparatus;

illuminating the lateral-flow chromatographic assay cassette to yield a detectable signal from the at least one reporter substance; and querying an interpretive algorithm stored in a computer readable format and electronically coupled to the handheld device, wherein the interpretive algorithm is configured for (i) calculating a calibration curve and the (ii) converting the detectable signal from the at least one reporter to a numerical value related to the presence or amount of the at least one analyte present in a sample.

2. The method of claim 1, wherein the capture ligand includes at least one of an antibody, an epitope, or a nucleic acid immobilized on the lateral-flow chromatographic assay cassette.

3. The method of claim 1, further comprising mixing the liquid sample with a dye conjugate prior to applying the sample to the lateral-flow chromatographic assay cassette, wherein the dye conjugate is configured to interact with at least one of the analyte of interest or the capture ligand to provide a visual readout related to the presence or concentration of the analyte of interest in the sample.

4. The method of claim 1, wherein the detectable signal includes at least one of emission, color intensity, reflectance, diffuse scattering, elastic light scattering, transmission, fluorescence, surface plasmon detection, Rayleigh scattering, electrochemical detection, conductivity, or absorbance.

* * * * *